United States Patent
Scherer et al.

(10) Patent No.: US 7,079,240 B2
(45) Date of Patent: Jul. 18, 2006

(54) PHOTONIC CRYSTAL LASER SOURCES FOR CHEMICAL DETECTION

(75) Inventors: Axel Scherer, Laguna Beach, CA (US); Marko Loncar, Somerville, MA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/794,071

(22) Filed: Mar. 5, 2004

(65) Prior Publication Data
US 2005/0110992 A1   May 26, 2005

Related U.S. Application Data

(60) Provisional application No. 60/452,268, filed on Mar. 5, 2003, provisional application No. 60/453,185, filed on Mar. 10, 2003.

(51) Int. Cl.
*G01J 3/30* (2006.01)
*G01N 21/41* (2006.01)
*G01N 21/00* (2006.01)
*H01S 3/08* (2006.01)

(52) U.S. Cl. .............. 356/318; 356/128; 356/432; 372/92

(58) Field of Classification Search ........ 356/300–334, 356/128, 432–442; 250/552, 573, 574, 428, 250/432 R, 435, 436, 458.1, 459.1, 461.1; 422/82.05–82.11
See application file for complete search history.

(56) References Cited

U.S. PATENT DOCUMENTS

| | | | |
|---|---|---|---|
| 6,466,709 B1 * | 10/2002 | Scherer et al. ............. | 385/15 |
| 6,781,690 B1 | 8/2004 | Armstrong et al. | |
| 6,785,432 B1 * | 8/2004 | Letant et al. .............. | 385/12 |
| 6,802,489 B1 * | 10/2004 | Marr et al. ........... | 251/129.14 |
| 2002/0062782 A1 * | 5/2002 | Norris et al. ................ | 117/3 |
| 2002/0068018 A1 * | 6/2002 | Pepper et al. .......... | 422/82.05 |
| 2002/0167984 A1 * | 11/2002 | Scherer .................... | 372/50 |
| 2004/0101861 A1 * | 5/2004 | Little et al. ................. | 435/6 |

OTHER PUBLICATIONS

T. F. Krauss et al., "Two-dimensional photonic-bandgap structures operating at near-infrared wavelengths," Nature, 383:699-702 (1996).

H. Mabuchi et al., "Quantum Networks Based on Cavity QED," Quantum Information and Computation, 1:7-12 (2001).

E. Miyai et al., "Localized Defect Modes with High-Quality Factors in a Photonic Crystal Slab on a Low-Index Dielectric Substrate," Jap. J. of Appl. Phys., 41:L694-L696 (2002).

(Continued)

*Primary Examiner*—Gregory J. Toatley, Jr.
*Assistant Examiner*—Gordon J. Stock, Jr.
(74) *Attorney, Agent, or Firm*—Gates & Cooper LLP

(57) ABSTRACT

A system, method and apparatus provide the ability to detect a chemical in an analyte. To detect the chemical, the invention utilizes a laser having an open cavity. A photonic crystal lattice structure having a defect defines a suitable geometry for such a cavity. The analyte is introduced directly into a high optical field of the cavity. Thereafter, the cavity is pumped and an emission from the laser is used to detect the presence of the chemical in the analyte.

30 Claims, 12 Drawing Sheets

OTHER PUBLICATIONS

J. Vuckovic et al., "Design of photonic crystal microcavities for cavity QED," Phys. Rev. E., 65:016608-1-016608-11 (2001).

T. Yoshie et al., "High quality two-dimensional photonic crystal slab cavities," Appl. Phys. Lett., 79(26):4289-4291 (2001).

H. G. Park et al., "Nondegenerate monopole-mode two-dimensional photonic band gap laser," Lee, Appl. Phys. Lett., 79:3032-3034 (2001).

H. Y. Ryu et al., "Square-lattice photonic band-gap single-cell operating in the lowest-order whispering gallery mode," Appl. Phys. Lett., 80(21):3883-3885 (2002).

M. Loncar et al., "Low-threshold photonic crystal laser," Appl. Phys. Lett., 81(15):2680-2682 (2002).

T. Yoshie et al., "Quanum dot photonic crystal lasers," Elect. Lett., 38(17):967-968 (2002).

O. J. Painter et al., "Room Temperature Photonic Crystal Defect Lasers at Near-Infrared Wavelengths in InGaAsp," J. of Lightw. Tech., 17(11):2082-2088 (1999).

J. Vuckovic et al., "Optimization of the Q Factor in Photonic Crystal Microcavities," IEEE J. of Quant. Elect., 38(7):850-856 (2002).

K. Okamoto et al., "Near-field scanning optical microscopy of photonic crystal nanocavities," Appl. Phys. Lett., in press, 82(11):1676-1678 (2003).

O. Painter et al., "Defect modes of a two-dimensional photonic crystal in an optically thin dielectric slab," J. Opt. Soc. Am. B, 16(2):275-285 (1999).

D.J. Harrison et al., "Micromachining a Miniaturized Capillary Electrophoresis-Based Chemical-Analysis System on a Chip", Science 261:895-897 (1993).

N.H. Chiem et al., "Monoclonal antibody binding affinity determined by microchip-based capillary electrophoresis", Electrophoresis 19:3040-3044 (1998).

J.F. Li et al., "Separation and Identification of Peptides from Gel-Isolated Membrane Proteins Using a Microfabricated Device for Combined Capillary Electrophoresis/Nanoelectrospray Mass Spectrometry", Anal. Chem. 72(3):599-609 (2000).

C.S. Effenhauser et al., "Integrated Capillary Electrophoresis on Flexible Silicone Microdevices: Analysis of DNA Restriction Fragments and Detection of Single DNA Molecules on Microchips", Anal. Chem. 69(17):3451-3457 (1997).

S.C. Jacobson et al., "High-Speed Separations on a Microchip", Anal. Chem. 66(7):1114-1118 (1994).

H.P. Chou et al., "A microfabricated device for sizing and sorting DNA molecules,"Proc. Nat'l. Acad. Sci. 96:11-13 (1999).

H. Morgan et al., "Large area traveling-wave dielectrophoresis particle separator",J. Micromech. Microeng. 7:65-70 (1997).

S. Fiedler et al., "Dielectrophoretic Sorting of Particles and Cells in a Microsystem", Anal. Chem. 70(9):1909-1915 (1998).

J.P. Brody et al., "Low Reynolds Number Micro-Fluidic Devices", In Proc. Of Solid State Sensor and Actuator Workshop, pp. 105-108. Hilton Head, Jun. 1996.

M.U. Kopp et al., "Chemical amplification: Continuous-Flow PCR on a Chip", Science 280:1046-1048 (1998).

L.C. Waters et al., "Microchip Device for Cell Lysis, Multiplex PCR Amplification, and Electrophoretic Sizing", Anal. Chem. 70(1):158-162 (1998).

P.H. Li et al., "Transport, Manipulation, and Reaction of Biological Cells On-Chip Using Electrokinetic Effects," Anal. Chem. 69:1564-1568 (1997).

A.G. Hadd et al., "Microchip Device for Performing Enzyme Assays", Anal. Chem. 69(17):3407-3412 (1997).

A.G. Hadd et al., "Microfluidic Assays of Acetylcholinesterase Inhibitors", Anal. Chem. 71(22):5206-5212 (1999).

A.Y. Fu et al., "A microfabricated fluorescence-activated cell sorter", Nature Biotech. 17:1109-1111 (1999).

M.A. Unger et al., "Monolithic Microfabricated Valves and Pumps by Multilayer Soft Lithography," Science 288:113-116 (2000).

T. Thorsen et al., "Microfluidic Large-Scale Integration," Science 298:580-584 (2002).

S.R. Quake et al., "From Micro- to Nanofabrication with Soft Materials," Science 290:1536-1540 (2000).

A. Fu et al., "An Integrated Microfabricated Cell Sorter", Anal Chem., 74(11):2451-2457 (2002).

H.-P. Chou et al., "A Microfabricated Rotary Pump", Biomedical Microdevices 3(4):323-330 (2001).

J. Liu et al., "A nanoliter rotary device for polymerase chain reaction," Electrophoresis 23:1531-1536 (2002).

C. L. Hansen et al., "A robust and scalable microfluidic metering method that allows protein crystal growth by free interface diffusion," Proc. Nat'l. Acad. Sci. 99(26):16531-16536 (2002).

N. Wu et al., "General methods for designing single-mode planar photonic crystal waveguides in hexagonal lattice structures," Optics Express, 11(12):1371-1377 (2003).

H. Mabuchi et al., "Quantum Networks Based on Cavity QED," Quantum Information and Computation, 1:1-6 (2001).

M. Loncar et al., "Nanocavity lasers detect chemicals," Laser Focus World, pp. 89-91 (2003).

J. Laserna, "An Introduction to Raman Spectroscopy: Introduction and Basic Principles," Raman Resource including Vibrational Spectroscopy, http://www.spectroscopynow.com/Spy/basehtml/SpyH/1.1181.6-1-2-0-0-news_detail-4797176735-322.00.html, pp. 1-6 (2001).

"An Introduction to Raman Spectroscopy: Current Capabilities of Raman Spectroscopy," Raman Resource including Vibrational Spectroscopy, http://www.spectroscopynow.com/Spy/basehtml/SpyH/1.1181.6-1-2-0-0-news_detail-4797176735-323.00.html, pp. 1-3 (2001).

The Photonics Directory, Photonics Dictionary: Definition for word(s) Q, http://www.photonics.com/dictionary/lookup/XQ/ASP/url.lookup/entrynum.4288/letter.q/pu./QX/lookup.htm, 1 pg. (2004).

The Photonics Directory, file://C:\DOCUME~1\jfeldmar\LOCALS~1\Temp\D22POTIK.htm, 1 pg. (2004).

The Photonics Directory, "Fabry-Perot Cavity," http://www.photonics.com/dictionary/lookup/XQ/ASP/url.lookup/entrynum.1790/letter.f/pu./QX/lookup.htm, 1 pg. (2004).

AllWords.com—Dictionary, Guide, Community and More, http://adams.allwords.com/word-eigen-frequency.html, 1 pg. (2004).

TechWeb: The Business Technology Network, "Fabry-Perot," http://www.techweb.com/encyclopedia/defineterm?term=FABRY%2DPEROT&exact=1, 1 pg. (2004).

M. Weschler, Howstuffworks "How Lasers Work," http://science.howstuffworks.com/laser.htm/printable, pp. 1-9 (2004).

C. Freudenrich, Howstuffworks "How Light Works," http://science.howstuffworks.com/light.htm/printable, pp. 1-10 (2004).

"Photonic crystals for cavity quantum electrodynamics," Research, http://www.its.caltech.edu/~jonw/Research.htm, pp. 1-2 (2003).

J. Williams et al., "Photonic Crystal Microcavities for Cavity QED," http://minty.caltech.edu/PBG/, pp. 1-6 (2003).

TechWeb: The Business Technology Network, "TechEncyclopedia: photon" http://www.techweb.com/encyclopedia/defineterm?term=photon, 1 pg. (2003).

TechWeb: The Business Technology Network, "TechEncyclopedia: photoelectric," http://www.techweb.com/encyclopedia/defineterm?term=photoelectric, 1 pg. (2004).

TechWeb: The Business Technology Network, "TechEncyclopedia: photonic," http://www.techweb.com/encyclopedia/defineterm?term=photonic, 1 pg. (2004).

TechWeb: The Business Technology Network, "TechEncyclopedia: wave-particle duality," http://www.techweb.com/encyclopedia/defineterm?term=wave%2Dparticleduality, 1 pg. (2004).

TechWeb: The Business Technology Network, "TechEncyclopedia: photonic crystal," http://www.techweb.com/encyclopedia/defineterm?term=PHOTONICCRYSTAL&exact=1, 1 pg. (2004).

TechWeb: The Business Technology Network, "TechEncyclopedia: dielectric," http://www.techweb.com/encyclopedia/defineterm?term=dielectric, 1 pg. (2004).

TechWeb: The Business Technology Network, "TechEncyclopedia: insulator," http://www.techweb.com/encyclopedia/defineterm?term=insulator, 1 pg. (2004).

* cited by examiner

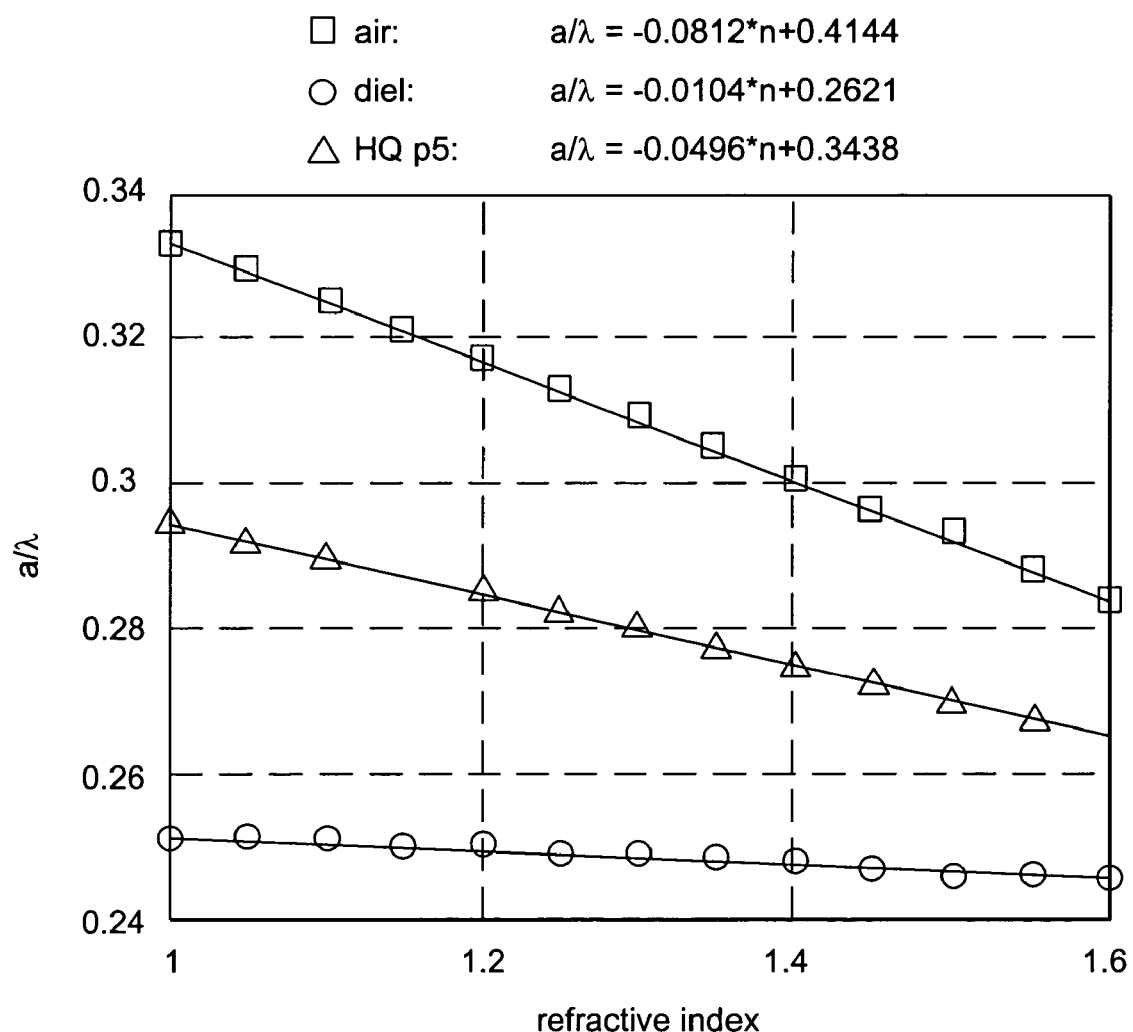

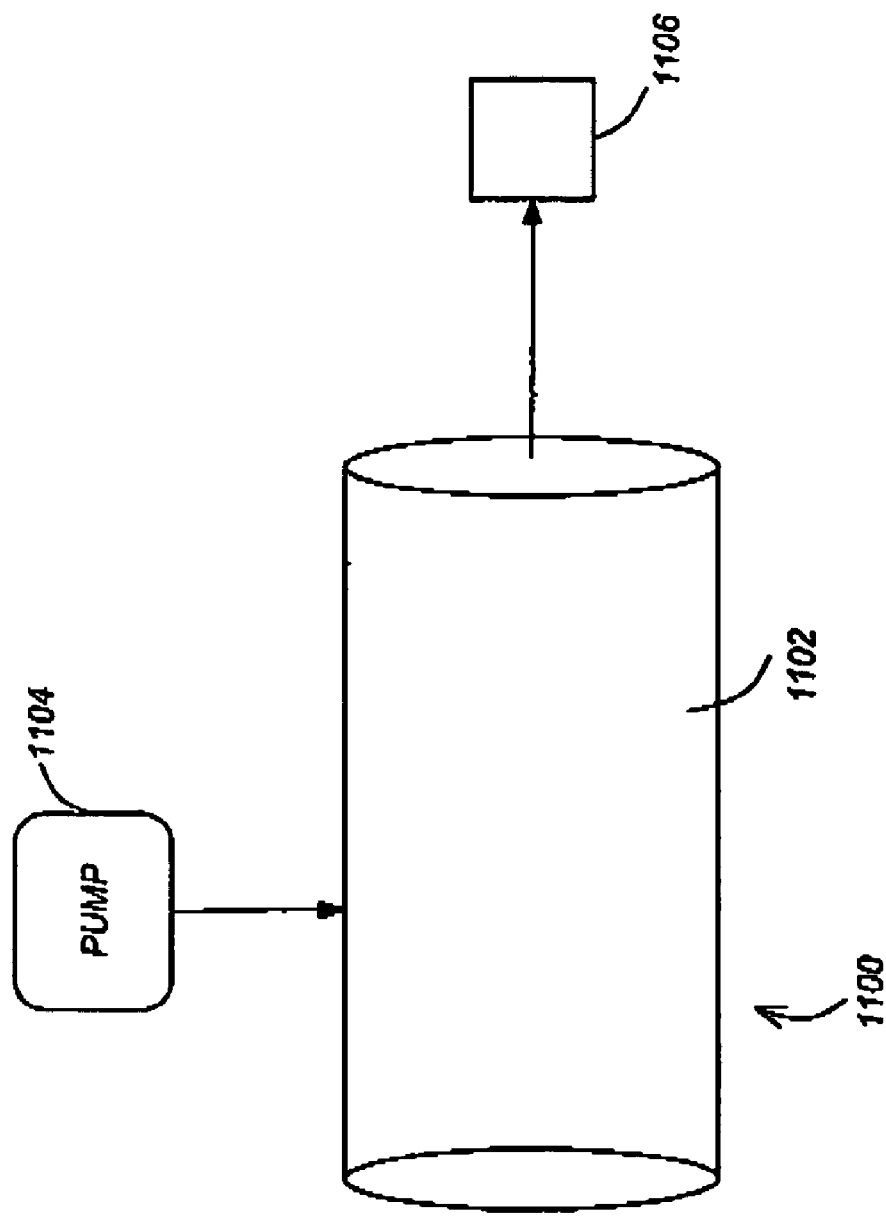

PHOTONIC CRYSTAL LASER SOURCES FOR CHEMICAL DETECTION

CROSS-REFERENCE TO RELATED APPLICATIONS

This application claims the benefit under 35 U.S.C. Section 119(e) of the following co-pending and commonly-assigned U.S. provisional patent application(s), which is/are incorporated by reference herein:

Provisional Application Ser. No. 60/452,268, filed on Mar. 5, 2003, by Marko Loncar and Axel Scherer, entitled "Photonic Crystal Laser Sources for Chemical Detection," and Provisional Application Ser. No. 60/453,185, filed on Mar. 10, 2003, by Marko Loncar and Axel Scherer, entitled "Photonic Crystal Laser Sources for Chemical Detection."

STATEMENT REGARDING FEDERALLY SPONSORED RESEARCH AND DEVELOPMENT

The invention was made with Government support under Grant No. BES-011949; ECS-9912039 awarded by the National Science Foundation. The Government has certain rights in this invention.

BACKGROUND OF THE INVENTION

1. Field of the Invention

The present invention relates generally to chemical detection, and in particular, to a method, apparatus, and article of manufacture for detecting chemicals using photonic crystal laser sources.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Various prior art techniques have been used to detect and determine the presence of a chemical in an analyte. An example of one such technique is the use of a semiconductor laser that is pumped such that the laser emission is projected into the analyte. The amount of refraction, emission, or spectra that is observed may then be used to determine the chemical composition within the analyte. However, such measurements may be inaccurate, require substantial amounts of analyte to perform the analysis, and may not provide sufficient sensitivity for detecting a particular substance.

Another example of a measurement technique is spectroscopy. Spectroscopy (such as infrared absorption spectroscopy [IR], or Raman spectroscopy) is a method often used to detect and identify substances (e.g., gases, liquids, or solids) such as toxic or explosive materials. To identify an unknown substance, the spectra (e.g., the wavelength and intensity) of light (that has been absorbed, emitted, or scattered) from the molecules of the unknown substance are measured. In this regard, the spectra of light provide a "fingerprint" that can be used to identify the molecules.

Spectroscopy utilizes the absorption, emission, or scattering of electromagnetic radiation by atoms or molecules (or atomic or molecular icons) to qualitatively or quantitatively study the atoms or molecules, or to study physical processes. To measure spectral reflectance, a variety of different types of spectrometers may be used. In this regard, spectrometers often record a spectrum on a detector at a focal plane after a light ray/beam proceeds through a series of lenses, apertures, stops, and diffraction gratings.

The construction of compact spectroscopic tools for the optical analysis of ultra-small (~$10^{-18}$ liter) sample volumes remains an important goal in the development of integrated microfluidics systems. Miniaturization of appropriate light sources and detectors can enable very compact and versatile "laboratory on a chip" devices, in which many analytical functions can be monolithically combined. One of the device integration platforms which is ideally suited to enable such integration of ultra-small and efficient optical components is the membrane based planar photonic crystal, defined in high refractive index contrast materials by standard lithography and semiconductor fabrication processes. A photonic crystal is a fabricated material with a spatially periodic dielectric constant, for example, a dielectric slab with a lattice of holes etched in it. Some lattice types can exhibit a photonic bandgap, a range of wavelengths of light for which propagation through the material in certain directions is not allowed. A defect in the lattice, for example, a missing hole, can give rise to localized modes with wavelengths within the photonic bandgap, thus acting as an optical cavity.

High quality optical cavities with mode volumes far below a cubic wavelength may be used to obtain very high optical field intensities from ultra-small laser sources. Until recently, the applications of planar photonic crystals have been restricted to large-scale integration of optical wavelength division multiplexing (WDM) components for telecommunications. Compact lasers, detectors, modulators, waveguides and prisms have been fabricated and demonstrated in semiconductor slabs of silicon, GaAs or InGaAsP [1]. These devices have been used to generate, concentrate and route light efficiently within nanophotonic chips. Discrete planar photonic crystal nanocavities with high quality factors and small mode volumes have also been applied to cavity QED experiments [2]. These take advantage of the strong overlap between a spectrally narrow light emitter placed into the intense electromagnetic fields of a high finesse optical nanocavity.

However, to date, photonic crystal cavities have not been used to provide sensitive detection of chemicals. Further, prior art spectroscopy has many limitations including requiring the use of large amounts of analyte and a lack of sensitivity in determining the presence of certain chemicals.

SUMMARY OF THE INVENTION

The invention provides the ability to utilize photonic crystal lasers that permit the introduction of analyte within the peak of the optical field of a lasing mode. Accordingly, the unique design of the laser cavity geometry (i.e., comprising photonic crystal) in combination with the ability to place the anlayte directly into the cavity provides the capability to conduct high-resolution spectroscopy with single-molecule sensitivity. In this regard, the nanocavity lasers of the invention may be used to perform spectroscopic tests on femtoliter volumes of analyte.

BRIEF DESCRIPTION OF THE DRAWINGS

Referring now to the drawings in which like reference numbers represent corresponding parts throughout:

FIG. 2B shows the dependence of the eigen-frequency of the lasing mode in accordance with one or more embodiments of the invention;

FIG. 11 is a laser structure used for detecting a chemical in accordance with one or more embodiments of the invention.

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

One or more embodiments of the invention define photonic crystal lasers that permit the introduction of analyte within the peak of the optical field of the lasing mode. Accordingly, the invention provides a novel cavity design combined with the introduction of analyte into the cavity.

Photonic crystal lasers may be with different ambient organic solutions. Further, nanocavity lasers can be used to perform spectroscopic tests on sub-femtoliter volumes of analyte, and photonic crystal lasers may be used for high-resolution spectroscopy with single-molecule sensitivity. In addition to precise measurement of the index of refraction, the high optical field in the laser sensor cavities may be used for Raman spectroscopy and absorption spectroscopy. In contrast to larger laser cavities, the photonic crystal lasers support only one or two modes and do not suffer from problems with mode-hopping associated with larger semi-conductor lasers.

Compact and robust chip-based spectroscopy systems may be built monolithically by integrating laser sources with filtered detectors in planar photonic crystal slabs. Sensors produced in this manner may be integrated with microfluidic systems that can deliver and react picoliter volumes of analyte. Further, similar lasers may be used for the visible and near-IR wavelength ranges from 600–1000 nm as well as wavelength ranges from 2000 to 10,000 nm by applying different materials systems and scaling the described geometry with the wavelength.

Technical Rationale

Embodiments of the invention use planar photonic crystal cavities in the development of chemical sensors, with high spectral resolution and excellent sensitivity to changes in the absorption or refractive index of their surrounding. By combining an unconventional cavity geometry with optical gain at 1550 nm, ultra-small sensor elements may be defined that can emit a very narrow spectrum. Since these are lithographically defined, such sources can easily be integrated into large arrays to perform biological and chemical analysis on extremely small reagent volumes with outstanding sensitivity.

Figure 1A:
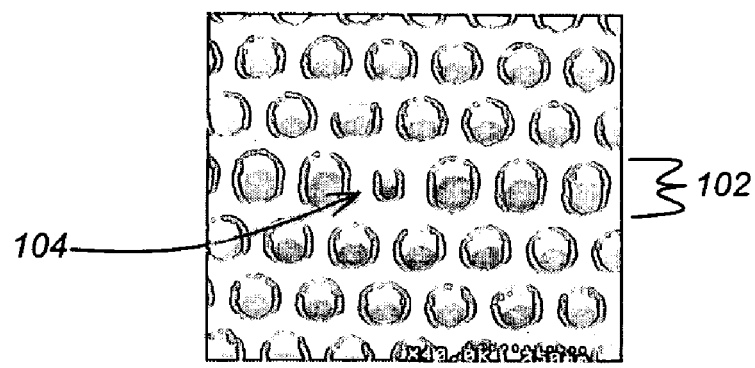
FIG. 1A illustrates a magnified view of an unconventional cavity geometry in accordance with one or more embodiments of the invention.

FIG. 1A illustrates a magnified view of an unconventional cavity geometry in accordance with one or more embodiments of the invention. As illustrated, the cavity is based on fractional edge dislocations 102 and distribution of $E_{amp1}$ in the case of High-Q mode (see detailed description below). Further, as illustrated, a single defect 104 is used in the cavity design.

Figure 1B:
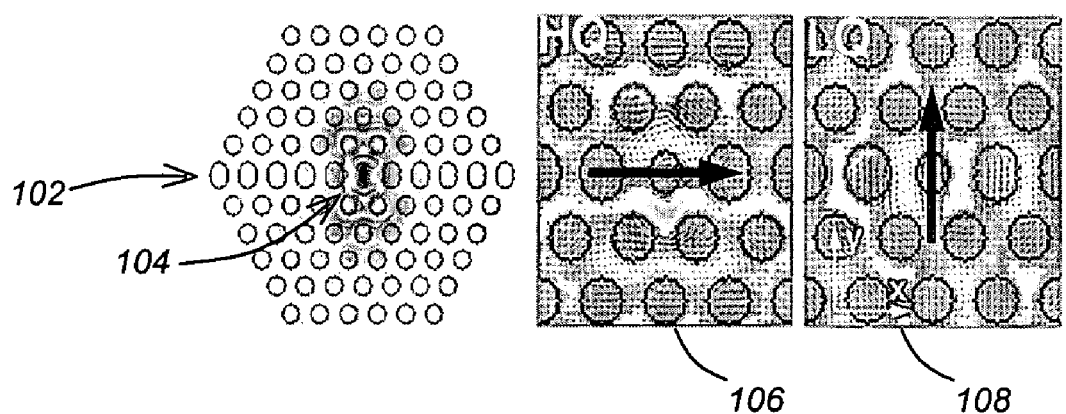
FIG. 1B illustrates the calculated field distribution of a photonic nanocavity laser sensor followed by two dipole modes supported in the cavity in accordance with one or more embodiments of the invention.

FIG. 1B illustrates the calculated field distribution of a photonic nanocavity laser sensor (i.e., for the magnified view of FIG. 1A) followed by two dipole modes supported in the cavity: mode profile 106 and polarization 108.

Laser Design

As described above, embodiments of the invention define a novel cavity geometry. The cavity geometry utilized to sense/detect the chemicals in an analyte is based on a single defect triangular lattice planar photonic crystal [2–11]. In addition to the introduction of a smaller hole 104 to define the optical cavity, a fractional edge dislocation 102 is introduced by extending the length of one of the rows of holes to break the symmetry of the optical cavity.

The prior art experimentally describes the advantages of such a structure, and have shown that it supports modes with both high Q [9] and small Vmode [12]. As used herein, Q refers to the figure of merit of a resonator defined by the average energy stored in the resonator divided by the energy dissipated per cycle. In this regard, the higher the reflectivity of the surfaces of an optical resonator, the higher the Q and the less energy loss from the desired mode.

When defined within InGaAsP (Indium Gallium Arsenic Phosphide) membranes, low-threshold room temperature lasers have also been defined [8]. The cavity design is shown in FIG. 1B and it can be seen that the energy of the mode is mostly confined to the central defect hole 104. In order to increase the interaction between light and the material within that hole, a larger defect hole diameter is preferred. However, increasing this hole reduces the gain provided by the light emitting quantum wells within the laser cavity and thereby increases the threshold of the laser. Therefore, a trade off between the optical overlap with the analyte cavity and the optical gain is needed. Such a problem may be addressed using numerically modeling.

The laser cavity may be defined using 3-D finite-difference time-domain modeling. The thickness of the slab with refractive index of 3.4 was d=0.75a, where a is the lattice parameter of the photonic crystal. The size of the holes which define the planar photonic crystal mirror surrounding the cavity was r=0.3a. A single defect donor cavity 104 in a triangular lattice photonic crystal without the fractional edge dislocation 102 is known to support two doubly-degenerate, linearly polarized, dipole modes [13] with rather modest quality factors of several hundred.

However, as the photonic crystal lattice is stretched by introducing a fractional dislocation, these modes start to interact, the degeneracy between them is lifted, and the quality factor of one of these modes is increased to over 6000. This optical Q can be separated into the vertical component ($Q_{vert}$), which accounts for all out-of-plane losses from the cavity, and the lateral component ($Q_{lat}$), which accounts for in-plane losses. The highest Q that can be achieved within a planar photonic crystal cavity is usually limited by $Q_{vert}$, since $Q_{lat}$ can be arbitrarily increased by lithographically adding more photonic crystal layers around the photonic crystal defect [13]. It is of interest to determine the change in this Q as the cavity is back-filled with reagents.

Figure 2A:
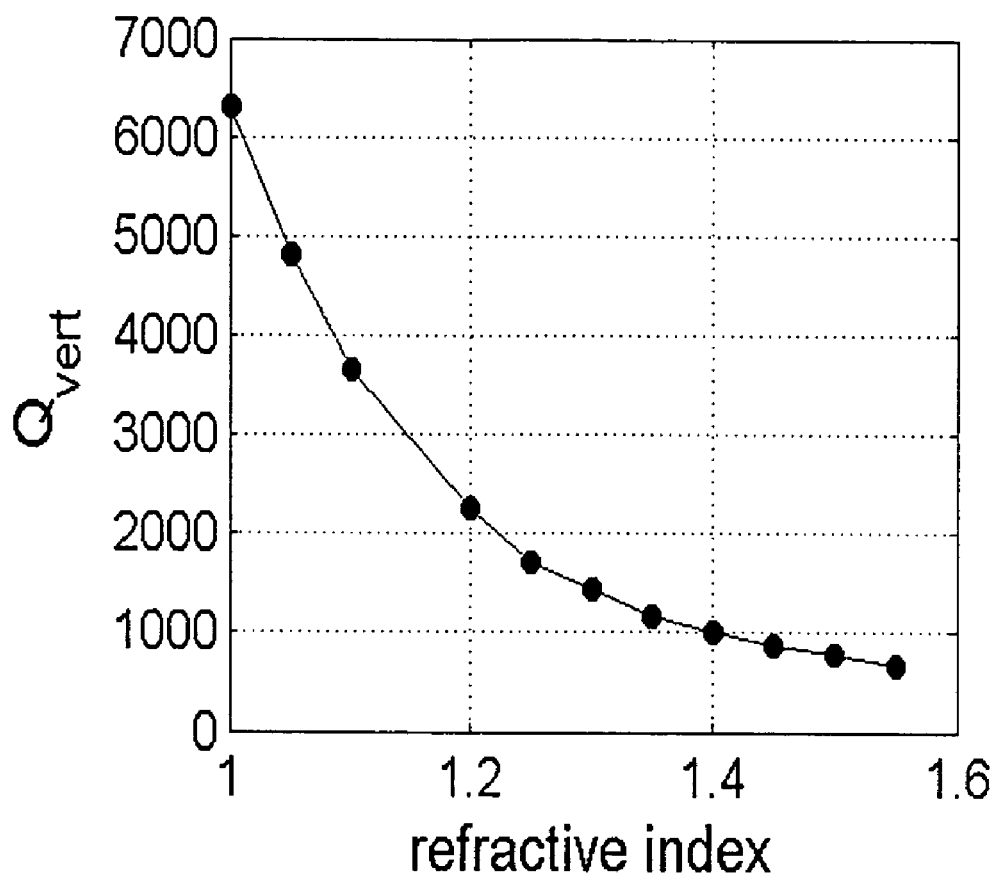
FIG. 2A illustrates the Q factor of HQ mode (p/a=25%) on the refractive index of an analyte in accordance with one or more embodiments of the invention.

FIG. 2A illustrates the Q factor of HQ mode (p/a=25%) on the refracive index of an analyte in accordance with one or more embodiments of the invention. From FIG. 2A, it may be observed that the highest Q (of above 6000) that may be achieved in the modeled cavity design occurs at an ambient refractive index n=1, and this value deteriorates as the refractive index of the ambient surrounding the photonic crystal cavity is increased. This decrease in Q is a result of the weaker vertical confinement of light by total internal reflection, and can be compensated for by increasing the thickness of the photonic crystal slab.

Another important figure of merit for evaluating the performance of a laser spectrometer is the gain provided by the active material to the lasing mode. As the defect hole diameter is decreased and the amount of dislocation is increased, a better overlap between the optical cavity mode and the quantum wells, and a decrease in the laser threshold may be expected. However, it is important in spectroscopy applications that the defect hole is large in order to obtain the desired interaction between optical cavity field and the reagent. Therefore, $r_{def}$=0.15a and p=0.25a may be used as a laser sensor design.

As described above, lasers may be immersed into solvents in order to investigate the properties of the analyte. Therefore, it is important to investigate the effects that refractive index of analyte (n>1) has on the eigen-frequency and Q of the laser resonance. FIG. 2B shows the dependence of the eigen-frequency of the lasing mode. It can be seen that Q values over 1000 can be achieved even when the laser is immersed in an analyte with refractive index $n_{analyte}$=1.4. It may also be seen that the frequency of the resonant mode, as well as the band edges of the PBG (photonic bandgap), depend linearly on the refractive index of the analyte. From linear fits of the dependence of the resonant frequency on the refractive index of the analyte ($n_{analyte}$), the sensitivity of the cavity may be estimated. Accordingly, the wavelength shift of the resonance should be approximately $\Delta\lambda\approx266 \cdot \Delta n$ for the cavity geometry used in the example (FIG. 1). The magnitude of the shift depends on the precise cavity geometry used and must be re-calibrated for each laser.

If it is assumed that the cavity is embedded in a typical polymer (n≈1.4) and below the lasing threshold, a change in refractive index that is still observable from cavity Q values would be $\Delta n$~0.002. That would provide a wavelength shift of $\Delta\lambda\approx0.54$ nm. On the other hand, once optical gain is introduced into the cavity, as in the case of the a laser spectrometer, the linewidth of emission is significantly narrowed, and therefore much higher sensitivities of $\Delta n$<<0.001 can be measured even in cavities with modest Q factors.

To demonstrate the above, photonic crystal nanolasers can be fabricated from InGaAsP quantum well material. Optical gain provided by four 9 nm thick, compressively strained quantum wells, may then be placed in the center of a 330 nm thick InGaAsP slab. The emission from the quantum wells is in the range of 1300 nm<λ<1600 nm, and these can be embedded within a free standing membrane, patterned with a photonic crystal lattice as shown in FIG. 1B. The precise emission wavelength can be controlled either by scaling the lattice parameter, or by changing the size of the defect hole 104 introduced into the lattice to form the cavity. The structures can then be tested using micro-photoluminescence approach, and optically pumped at room temperature with 30 ns pulses of 3 μs periodicity ($\lambda_{pump}$=830 nm). Further details of fabrication procedure and experimental methods can be found in Reference [8].

Chemical Sensing

Embodiments of the invention utilize low-threshold laser cavities as chemical sensors. The porous cavity design of the invention permits the introduction of analyte directly into the high optical field of the laser cavity. When the overlap between that introduced analyte and the optical field generated in the laser cavity is optimized, the sensitivity of a fabricated nanocavity sensor can be maximized. Moreover, the ultrasmall mode volume of the lasers permits the sensitivity to optical changes within sub-femtoliter volumes. Photonic crystal nano-cavities can support high optical fields with very small mode volumes ($V_{mode}$), and such structures may be ideal for the analysis of reagent volumes below $10^{-18}$ liters. This enables the sensing and analysis of individual organic molecules or self-assembled quantum dots, and offers a unique opportunity to achieve strong interaction between light and molecules on a nano-scale level.

Figure 3:
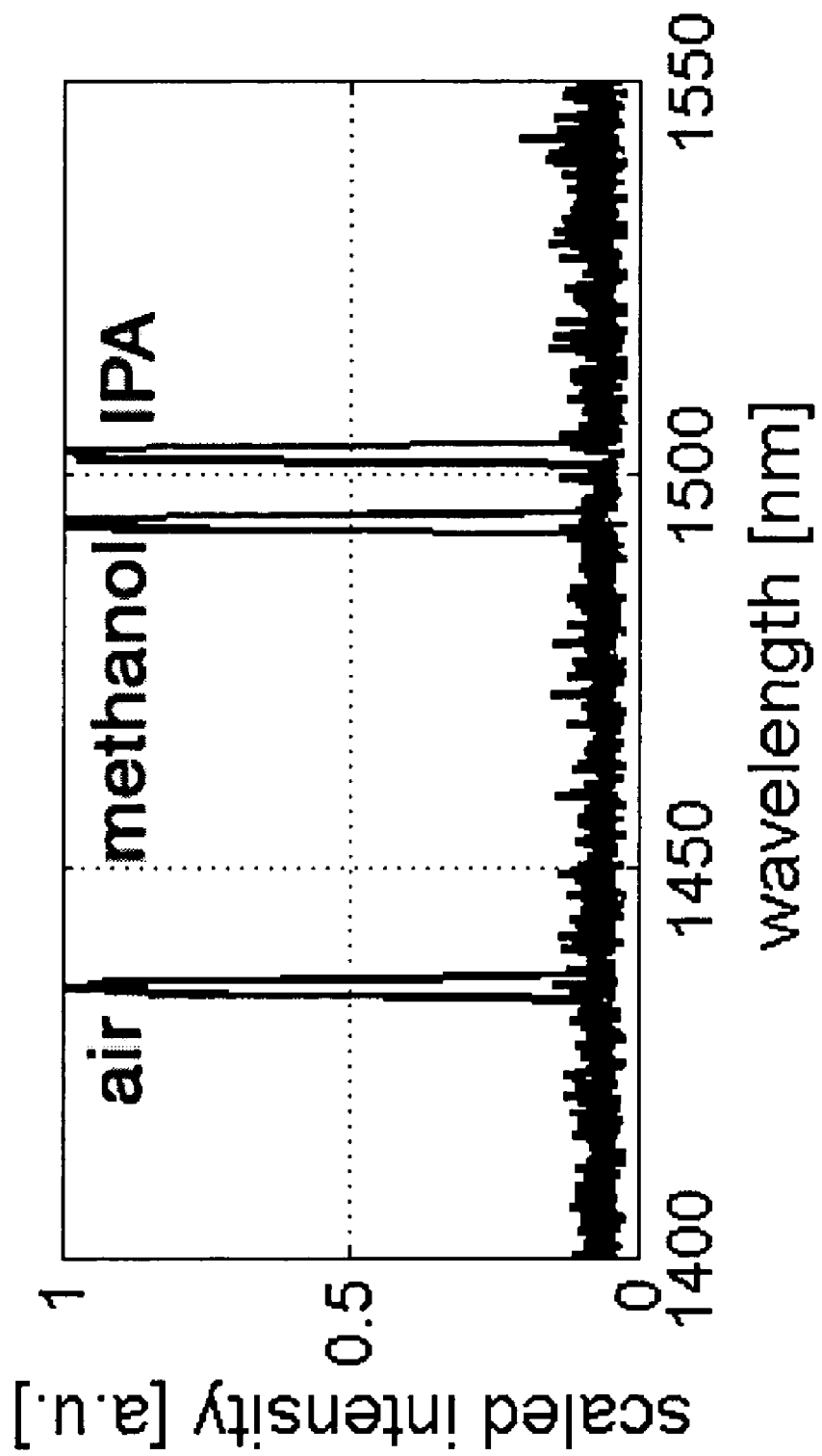
FIG. 3 illustrates the measured laser spectra of a photonic nanolaser sensor when filled with air, methanol, and IPA in accordance with one or more embodiments of the invention.

The introduction of absorbing or fluorescing molecules into such cavities may also have a large influence on the optical signature, and in turn the high fields obtained can be used to excite nonlinear effects and can be used for spectroscopy on the cavity contents. Further, when properly designed, room temperature lasers can operate within an analyte, and changes in refractive index of the material within the laser cavity can be optically detected. For example, FIG. 3 illustrates the measured laser spectra of a phontonic nanolaser sensor when filled with air, methanol, and IPA.

The simplest method of optically sensing ambient material uses the laser spectrum to determine the cavity length and thus the refractive index of a reagent within the cavity. This method uses the wavelength shifts in the laser spectrum when the laser is immersed into a solution or exposed to a material to measure its refractive index. In this method, the sensitivity of the sensor depends on the smallest change in refractive index that can be optically detected. In passive devices, this is related to the width of the cavity resonance Fabry-Perot peak which in turn is determined by cavity quality Q, and can be as small as ~0.2 nm in the presented cavity design.

However, a laser linewidth can be much narrower than the Fabry-Perot cavity peak, and even smaller shifts in the lasing wavelength can be detected by taking advantage of the spectral narrowing from stimulated emission above the laser threshold. To test the influence of a change in ambient refractive index on the laser spectrum of a cavity, photonic crystal lasers may be back-filled with isopropyl alcohol and methanol.

Figure 4:
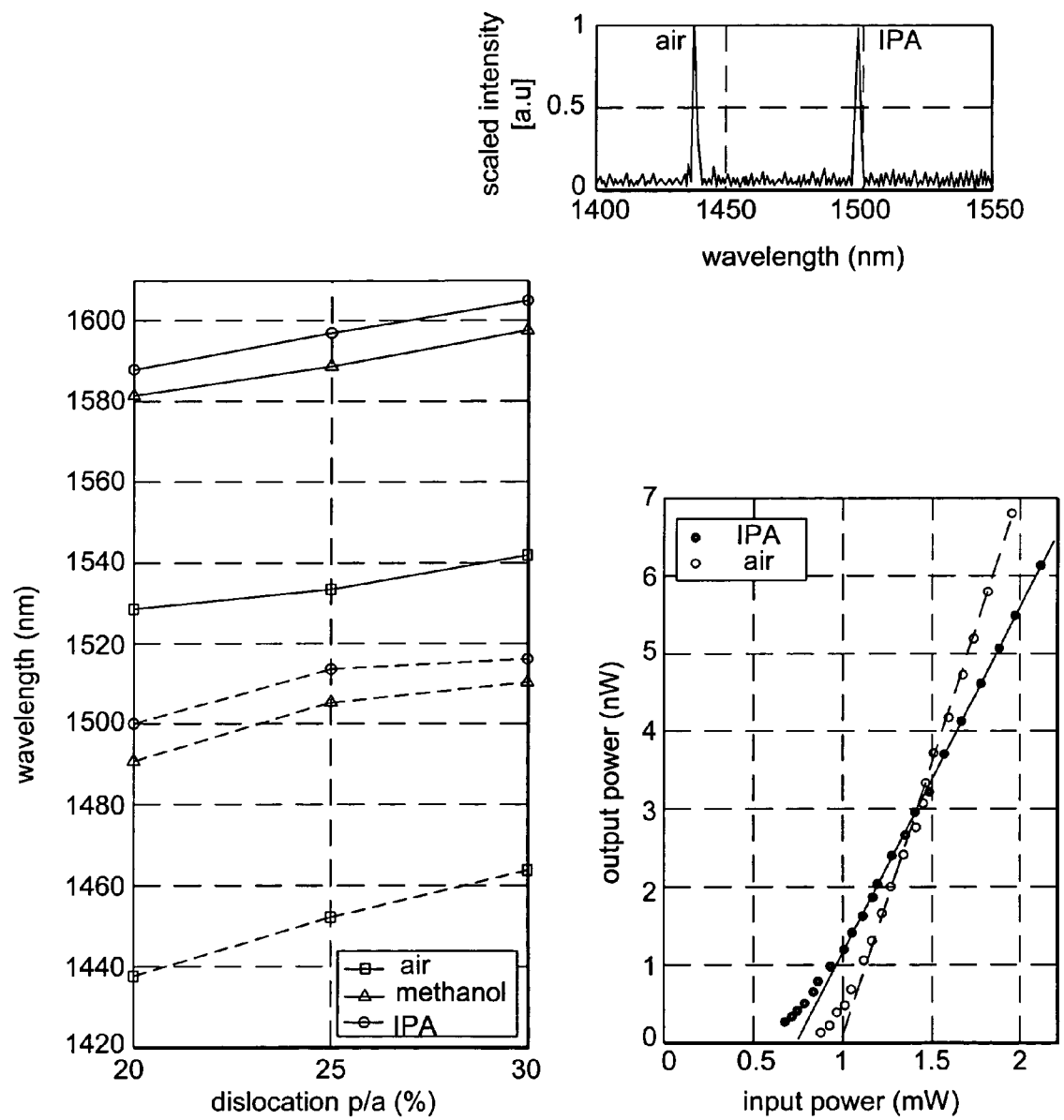
FIG. 4 shows the position of the resonances from six different lasers after immersion in air, isopropyl alcohol (IPA) and methanol in accordance with one or more embodiments of the invention.

FIG. 4 shows the position of the resonances from six different lasers after immersion in air, isopropyl alcohol (IPA) and methanol. It can be seen that wavelength shifts of up to 67 nm can be observed when a cavity is immersed in IPA. This red-shift corresponds to a change in refractive index from 1.0 to 1.377, and yields roughly 1 nm spectral shift for a 0.0056 change in refractive index. When IPA is replaced with methanol (n=1.328), the laser resonance experiences a blue shift of ~9 nm, which is again in good agreement with predicted shift of ~13 nm from theoretical predictions (FIG. 2B).

The dependence of the cavity resonance wavelength on the lithographic laser geometry, particularly the lattice constant and the dislocation in the photonic crystal cavity may also be demonstrated. Resonances experience red shifts of ~80 nm when the periodicity is changed from a=446 nm (dashed lines) to a=460 nm (solid lines). Such shifting confirms that it is possible to lithographically adjust the emission wavelength to ensure an overlap of the cavity resonance peak with the InGaAsP quantum well emission gain curve even when the cavities are immersed in a reagent.

Laser threshold curves before and after immersion into alcohol are also presented in FIG. 4. After immersion, the laser threshold power for the cavity measured was reduced since the emission wavelength was shifted to match the maximum gain of the quantum wells. However, the differential quantum efficiency of the immersed cavity is slightly lower, which may reflect the lower laser cavity Q after immersion.

Dense Integration of Laser Sensors

Structures may also be tested with different defect hole radii ($r_{def}$) within the same photonic crystal slab in order to explore the integration multi-wavelength photonic crystal lasers with lithographically predetermined spectra. These devices are particularly interesting as compact multi-wavelength light sources, but are also useful if many reactions have to be monitored at the same time. Individual reactions can be observed in laser cavities which have predetermined spectral signatures, and optically read by observing changes in the collective spectrum of a multiwavelength laser array.

Figure 5:
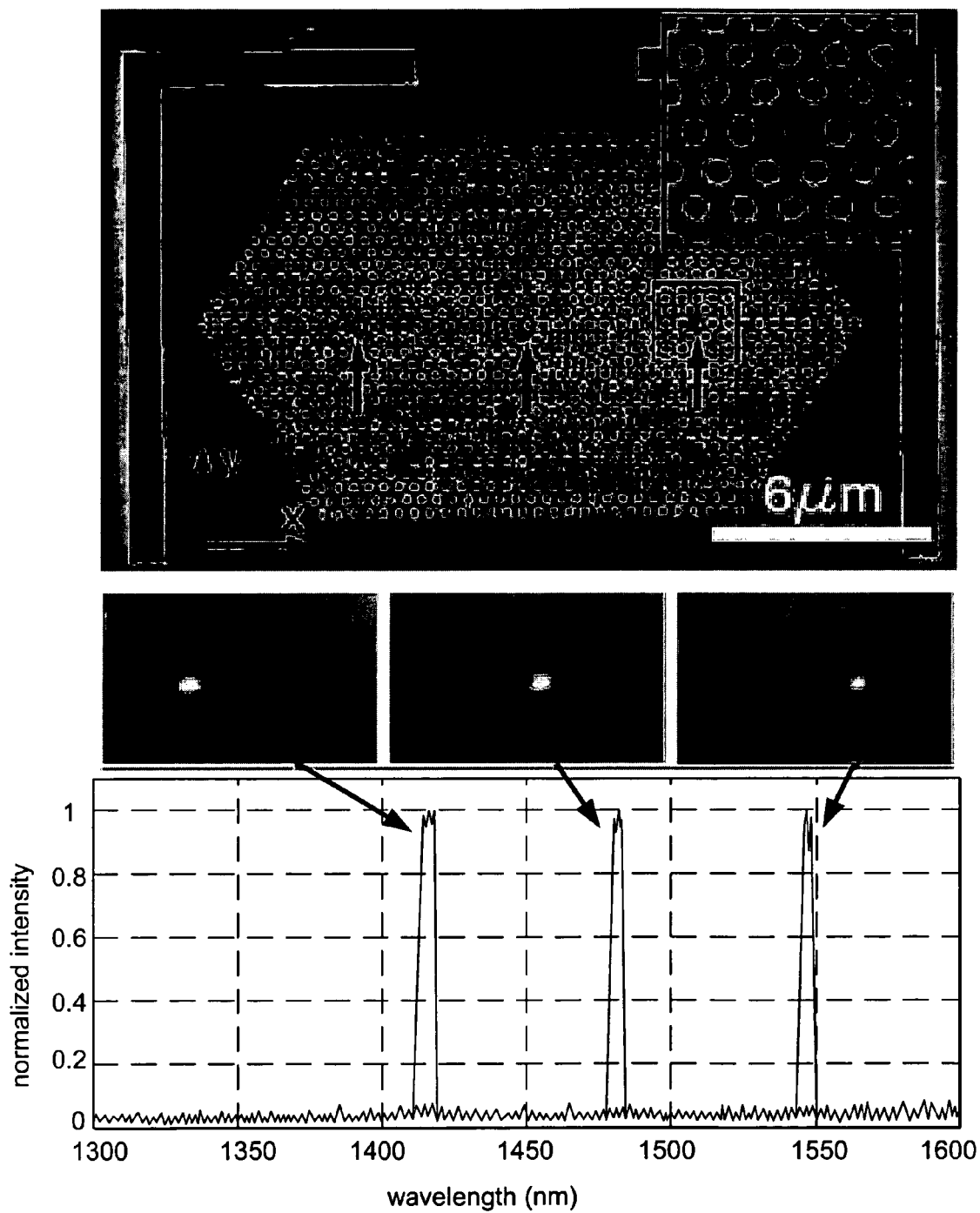
FIG. 5 illustrates both the structure and accompanying spectra of three optical cavities fabricated within a common photonic crystal slab in accordance with one or more embodiments of the invention.

FIG. 5 illustrates both the structure and accompanying spectra of three optical cavities fabricated within a common photonic crystal slab with lattice constant a=446 nm and r=134 nm. The fabricated structure consists of three cavities integrated within the same PPC mirror. Defect holes are indicated by arrows, and their size increases from right to left. The sizes of the defect holes which define the optical cavities were varied from $r_{small}$=74 nm, $r_{mid}$=85 nm and $r_{big}$=97 nm, and a detailed view of one of the cavities is shown in the inset. The distance between the three cavities is 10 lattice periods or ~4.5 μm. To measure these lasers, the cavities were pumped individually, and well-confined spectra were obtained from each of these cavities. The lasing wavelength of these cavities can be tuned from 1420 nm (for $r_{big}$) to 1550 nm (for $r_{small}$). FIG. 5 also illustrates the resonances detected in each cavity. Mode experience blue-shift as the size of the defect hole increases. Positions of the pump beams are also shown.

By using adjacent resonator cavities, the integration of light sources with detectors is also possible, since InGaAsP quantum well material can be used both for the generation of light, as well as for the detection of light. Filtered photonic crystal nanocavity detectors can be included to monitor the output of adjacent laser diodes, as long as the detector resonance wavelength coincides with the lasing wavelength. By monitoring the intensity of the detector signal, it is possible to observe small changes in the laser emission wavelength. The invention demonstrates both the integration of multiple laser cavities that can be back-filled with analyte and used as refractive index probes, as well as their interrogation with wavelength-matched photonic crystal nanocavity detectors which can be fabricated in very compact tandem sensor systems.

Photonic Crystal Laser Chemical Detection Use

The narrow emission lines from laser cavities with small mode volumes (~$10^{-17}$ –$10^{-18}$ liters) provide excellent opportunities for chip-based integration of optical spectroscopy systems. Such lasers may be operated in various solvents. Further, shifts in the refractive index of the ambient material surrounding the laser cavities can be measured by monitoring the laser spectrum. Small changes in the refractive index or absorption can be detected within femtoliter volumes of reagent, and such devices can be integrated into large arrays to permit the simultaneous analysis of many reagents. However, the problems of reading out the signals for compact monitoring and sensing systems are still formidable. Nonetheless, if on-chip read-out of the signals is possible, and if such lasers can be demonstrated in spectral ranges where direct excitation of molecular absorption and dye fluorescence are possible, the proposed photonic crystal laser may provide an unsurpassed spectroscopic capability in both size and resolution.

Embodiments of the invention also present methods for on-chip integrated readout and analysis, as well as laser spectrometers with materials systems that will allow shorter wavelength operation. Since InGaAsP can serve both as a laser gain material as well as a material for light detection, it is possible to develop and use compact and integrated spectroscopy systems for detection of chemical and biological molecules. Such systems may be similar in principle to optical communications opto-electronic integrated circuits (OEICs), but do not suffer from the severe requirements of high speed and low insertion loss needed by telecommunications systems.

Since the lasers described herein are intended for biochemical sensing by backfilling the defect hole in the photonic crystal cavity with reagent, absorption and Raman spectroscopy can also be conducted for the analysis of chemicals within the nanolaser cavity. Moreover, since the optical field intensity is optimized to be highest in the center of the microfabricated hole containing the reagent, the optical field generated in the laser cavity can be used to optically trap materials (quantum dots, metallic particles, and even large molecules) of higher refractive index than the solvent surrounding the cavity.

On-Chip Laser Interrogation

The simplest method for using the proposed laser to analyze reagents is to measure the refractive index, which in turn can be monitored by the emission wavelength of the laser. Without integration, this measurement requires a spectroscopic read-out system with a high spectral resolution, typically obtained from a grating-based spectrometer. Apart from the large volume and complexity of such systems, it is more difficult to obtain high resolution with low insertion loss from light scattered from the top surface the photonic crystal laser than to tap into the in-plane lasing mode within the photonic crystal. Therefore, integration of detectors and lasers can be of great interest for active materials systems. It is possible to design tandem laser/detector systems to determine the laser wavelength.

Figure 6:
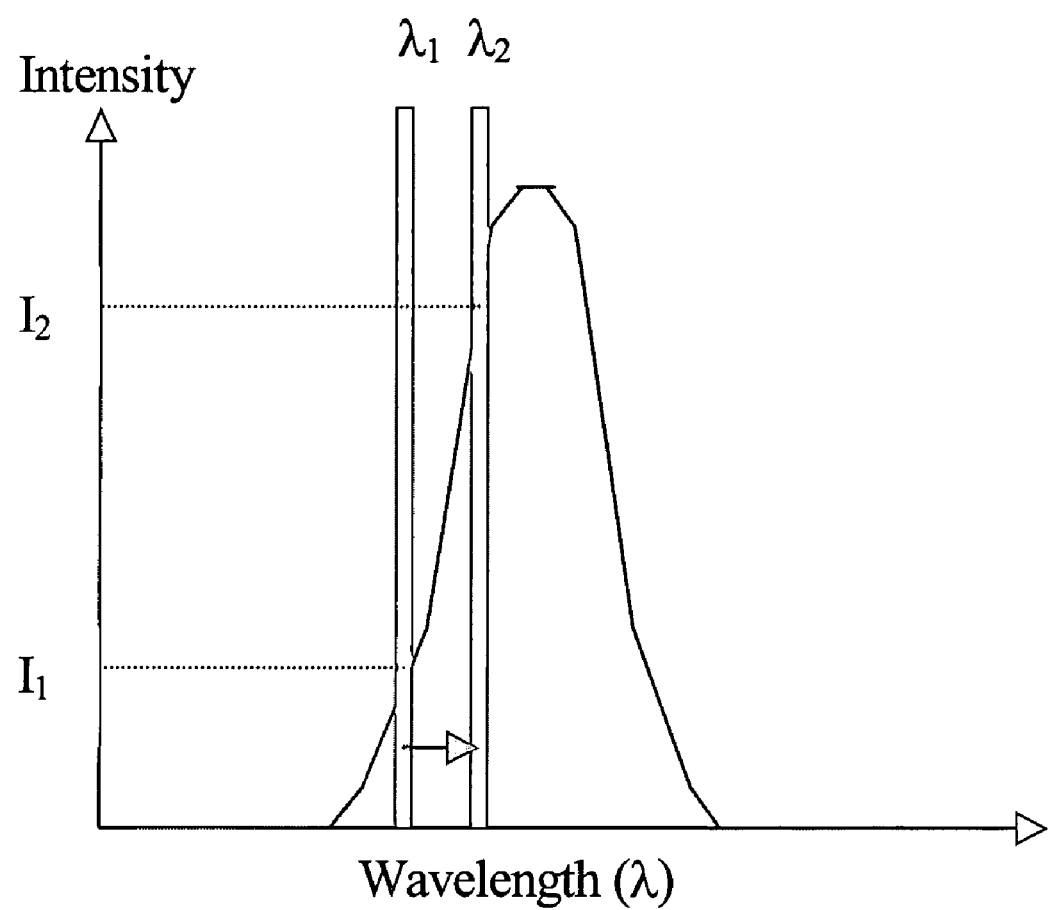
FIG. 6 illustrates the interrogation of the wavelength shift in a laser (blue) with a cavity enhanced detector in accordance with one or more embodiments of the invention.

FIG. 6 illustrates the interrogation of the wavelength shift in a laser (blue) with a cavity enhanced detector. A cavity-enhanced photodetector with a modest Q value is lithographically tuned to the emission wavelength of the emitting laser. In many respects, the filtered detector uses a similar nanocavity as the laser, except that it is reverse biased. A photo-induced signal proportional to the optical power coupled into the detector resonance peak is thus obtained. In a digital system, the detector cavity can be tuned to the lasing frequency and any change in laser wavelength detunes the two wavelengths and turns off the detector signal with a very high contrast.

The invention may utilize a detection approach in which small changes in laser frequency (from $\lambda_1$ to $\lambda_2$) are converted into readable changes in detector current (from $I_1$ to $I_2$). For such a system, the contrast obtained is related to the cavity Q of the detector. After a simple calibration, a change in measured electrical detector signal can be related to a corresponding shift in lasing wavelength, a change in the laser cavity length and thus a change in the refractive index within the cavity. In this measurement, it is assumed that the laser power is constant, that the detector window and the emission frequency of the laser and the detector overlap, and that the detector window remains constant during the measurement. These assumptions can be satisfied within an appropriately designed microfluidic or gas monitoring system, as detailed below.

Laser/detector tandem systems may also be built, integrated within the same photonic crystal slab containing active InGaAsP nanocavities, in which lasers are either optically or electrically pumped, and detector signals are electronically read out. A simple system can measure the refractive index and operate in either liquid or gaseous environments at room temperature, with excellent sensitivity provided by the ultra-small mode volumes of the cavities and the narrow spectrum of the laser. This system may be designed for optimal coupling of light from the laser into the detector, both lithographically aligned to ensure minimal insertion loss.

The detector can be designed without a void within its optical cavity, rendering its resonance frequency much less sensitive to ambient changes in the refractive index, and the measurement resolution is ultimately governed by the linewidth of the laser source, determined by the spectral narrowing through stimulated emission.

Changing the Spectral Range of Photonic Crystal Lasers

Spectroscopy for chemical detection of biological analysis is typically performed in the UV/Visible and the mid-IR wavelength ranges. This is a result of the availability of sources, detectors, and fluorescent dyes, but is also determined by the energy ranges at which bonds and molecular vibrations of molecules are excited. The 1.55 µm range, although convenient from the availability of efficient laser material, is not usually considered to be an interesting range for direct absorption measurements. Apart from some exceptions, such as sugars and acetylene which absorb in the near-IR, and the generally undesirable absorption of light in aqueous solutions due to the OH excitation peak at 1.41 µm, the 1.2–2.1 µm window provided by the InGaAsP lasers (of the present invention) may only have few applications in direct absorption measurements. On the other hand, the determination of the refractive index may be a very selective sensing approach even at such wavelengths.

Photonic crystal lasers of the invention may be used in materials systems other than InGaAsP. Further, a cavity enhanced detector in shorter wavelength ranges may also be provided. An additional benefit from reducing lasing wavelength is the improvement of the Raman excitation efficiency of molecules, which is typically inversely proportional to the pump wavelength. Lower wavelengths are therefore desirable from the point of view of higher efficiency Raman peak generation, but also provide cavities with smaller absolute mode volumes. For example, a shift from 1550 nm (InGaAsP/InP) to 690 nm (InGaP/InGaAlP/GaAs) corresponds to an over 10-fold reduction in sampling mode volume of the reagent in the cavity (to significantly below $10^{-17}$ liters). This geometric factor in turn can lead to an increased sensitivity to single molecules within that volume.

The present cavity design, with Q values up to 7000, may permit the definition of optically pumped lasers in visible light emitting materials systems. Tests have confirmed that carriers in InGaP/InGaAlP quantum wells, lattice matched to GaAs, suffer from only modest surface recombination, which permit the definition of ultra-small and highly efficient photonic crystal lasers in the 600–700 nm wavelength range.

Laser sources in the InGaN/GaN/AlGaN materials system may also be used, emitting in the blue and green (350 nm<$\lambda$<500 nm). While photonic crystal cavities in InGaN/GaN quantum wells may be defined, the vertical confinement of light may be limited by the relatively small refractive index contrast available between InGaN and AlN. To provide good confinement of an optical mode, anisotropic and isotropic selective etching methods may be used to enable the definition of blue optically pumped InGaN laser cavities, with sampling volumes as small as $10^{-18}$ liters.

One key advantage of such a sensor application is that it is not necessarily desirable to electrically pump the laser sources. Optical pumping, through elastomeric fluid channels and the solvents inside, may be the most convenient method for actuating the lasers. Further, electronic circuitry may be required for measuring the photovoltaic or photocurrent detector response, and problems with carrier mobilities, heating, light re-absorption, -Auger and surface recombination are far less significant in the filtered detectors than in low-threshold lasers. Accordingly, the invention uses small mode volumes and the high fields in the laser cavities to analyze ultra-small reagent volumes.

Decoration of Molecules and Optical Tweezing

Laser sensors may also be used to conduct fluorescence, luminescence and absorption sensing of single molecules after their decoration with fluorescent dyes, self-assembled quantum dots, or a nanometallic plasmon particles. Photonic crytsal lasers that can emit in the near near-IR, may be used for fluorescence purposes, as efficient two-photon absorption and fluorescence dyes have been developed for high resolution biological imaging. If specific molecules of interest are tagged with such dyes, visible signals can be observed when the decorated molecules enter the laser cavity.

Self-assembled PbSe and PbS quantum dots can also be used to decorate molecules of interest, and serve as luminescence indicators (i.e., as indicators for whether the molecules of interest are in the cavity that is then used to perform optical spectroscopy). Similarly, lasing in the cavity can be quenched if molecules tagged with absorbing nanoparticles, such as plasmon scatterers are introduced into the nanocavity.

The large optical field within the center of the laser sensor cavity can also hold samples in place during the analysis through optical tweezing, as long as the material of interest has a higher index of refraction than the ambient solvent. Thus, nanoparticles will be attracted to the center of the optical cavity and kept in place through the optical field. This provides the opportunity to place reagents into the optical cavity, and to hold them in place while performing spectroscopic observation of a reaction between that reagent and molecules of interest. It also provides a mechanism for scavenging single molecules of interest in very dilute solutions and concentrating these in the optical nanocavities—artificially improving the concentration sensitivity of the sensor systems.

The ultra-small mode volumes of the lasers result in high spontaneous emission coupling efficiencies (of approximately 80%), which translates into efficient pumping of the lasing mode by the quantum wells providing gain. This spontaneous emission coupling efficiency supports very high modulation rates, and presents the opportunity to perform pulsed measurements on delicate organic samples, avoiding bleaching and chemical deterioration of the molecules of interest.

When a metallic nanoparticle is introduced into an optical laser cavity, two effects may combine to generate extremely high electromagnetic fields. The small mode volume of the laser cavity ensures high optical fields, and these in turn excite plasmon modes in appropriately designed gold or silver nanoparticles. The high fields from the surface plasmon particles in turn provide Raman signatures of molecules attached to the metal colloids similar to those found in surface enhanced Raman spectroscopy (SERS), a technique which has long held the promise for single molecule spectroscopy. Further, SERS may be integrated into a laser cavity, to observe Raman effects at very high optical fields.

Laser Tuning, Self-Modulation and Switching

Since the above-described lasers can be operated after back-filling with a variety of materials, it is possible to insert photorefractive materials into the cavity. This presents the opportunity for switching, tuning and modulation. Accordingly, in embodiments of the invention, optically active polymers may be inserted, that have fairly low refractive indices and can be introduced into the cavities by spinning, dipping and subsequent electrostatic poling if required, into the nanocavities.

Of particular interest is the self-modulation or Q-switching of the nanolasers with photorefractive material. In such a device, the high field intensities and the efficient modal overlap between electromagnetic field and nonlinear polymer may assist in defining small active devices in which the lasing mode and cavity Q are tuned to modulate above and below lasing threshold.

Since the cavity may only support one or two modes, self-modulation with good contrast can be measured, since energy is not simply swapped from one mode to another. Another technological opportunity arises from the coincidence of recently developed high quality and very fast optically active polymers, such as chromophores, and the unconventional laser design. Fast self-modulating lasers may be designed as well as ultra-fast optical switches for bit-switching in communications and optical computing systems using the nanocavities.

Integration with Microfluidics

Ultra-small laser cavities lend themselves to the rapid integration with microfluidic systems. Fluidic "circuits" may be fabricated that can be used to manipulate and react sub-picoliter volumes on a chip. Valves and pumps may also be used in a multi-layer soft lithography (MSL) process within RTV silicone elastomer, that has been demonstrated for cell sorters, enrichment chips and multi-well reaction chips with over 1000 monolithically integrated valves. Embodiments of the invention integrate the optical spectroscopy tools within fluidic circuits. Valves, which may be based on pneumatic actuation, provide dead volumes of 1 picoliter, and can be actuated millions of times, and shift register addressing techniques may use the lithographic geometry of the pneumatic channels to leverage 18 input lines into over 1000 operations on the fluidic chips.

Since the introduction of the first microfabricated electrokinetic analytical device in 1991 [14], much work has been focused on using electrokinetic forces to separate ionic species such as peptides and DNA fragments through capillary electrophoresis [15–20]. Gradually, it has become apparent that the true potential of microfabricated devices lies in the ability to integrate a complete analysis system "on chip".

The invention provides such a complete analysis system in a microfabricated device that may perform more than just separation and detection. This "lab on a chip" may integrate functionalities such as sample handling, mixing, incubation, sorting, transportation, recovery, and automation. Thus, other means for controlling fluid flow within microfabricated devices have been considered. Dielectrophoresis [21, 22] and pressure switching [23] may be used to create valveless switches for separation of particles and cells within microchannels. Spatially fixed temperatures zones may also allow incubation at various regions in the microchannels [24]. Multiple ports and plugs dispense and dilute reagents for enzymatic reactions [25,26]. These advances in integrated analysis systems provided the opportunity for chips that can perform enzymatic assays [27,28], immunoassays [29,30], polymerase chain reaction [24,32] and cell sorting [21,29].

However, realizing the lab on a chip vision requires a high degree of integration of these individual elements. A major obstacle hampering progress has been the lack of scalable plumbing. While electrokinetic flow and direct pressure manipulation are suitable for simple devices, they do not scale well to more complicated devices. This problem may be solved through active integrated nanofluidic valves and pumps using multilayer soft lithography [30]. These valves allow for the manipulation of nanoliters and even picoliters of fluid [22] and are scalable to Large Scale Integration (LSI) densities [31].

Multilayer soft lithography (MSL) is a micromachining technique that exploits the elasticity and the surface chemistry of silicone elastomers in order to create monolithic valves within nanofluidic devices [30]. This technique is based on the rapid prototyping and replica molding techniques of soft lithography. A monolithic chip can be made of multiple layers of elastomeric channels, each layer having been cast from a microfabricated mold.

Figure 7:
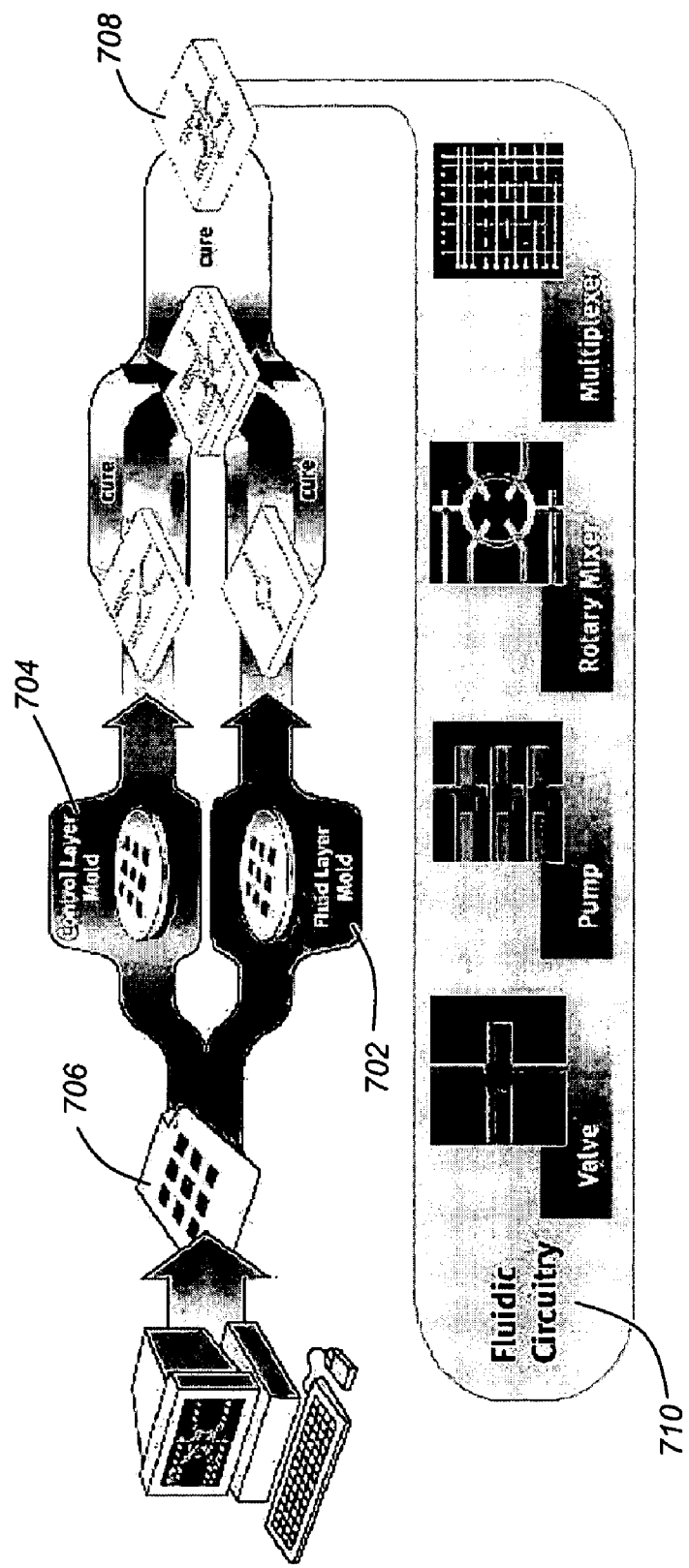
FIG. 7 illustrates a schematic diagram of how the MSL process is used to create nanofluidic chips in accordance with one or more embodiments of the invention.

FIG. 7 illustrates a schematic diagram of how the MSL process is used to create nanofluidic chips. In a typical two-layer system (as illustrated in FIG. 7), the bottom layer 702 consists of fluidic channels where the sample will be introduced and manipulated. The top layer 704 has control channels by which the valves will be pneumatically actuated. When pressurized air or nitrogen 706 is introduced into a control channel 704, the thin membrane between the two channels 702 and 704 is deflected downward, sealing off the fluidic channel 702. In this way, a leakproof active valve 708 with moving parts (illustrated in the fluidic circuitry 710) is created. The simplicity and flexibility in multilayer soft lithography allows for a high degree of integration of these plumbing units.

Figure 8A:
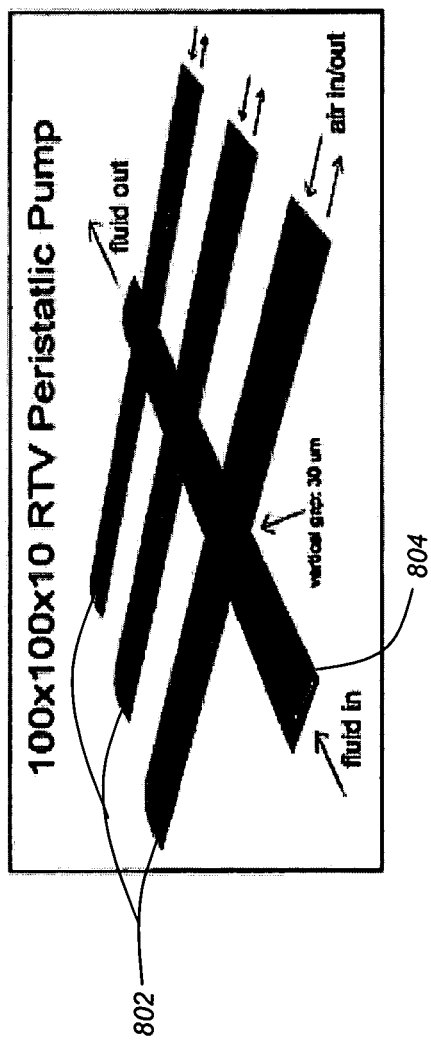
FIG. 8A illustrates a schematic diagram of a nanoliter pump in accordance with one or more embodiments of the invention.
Figure 8B:
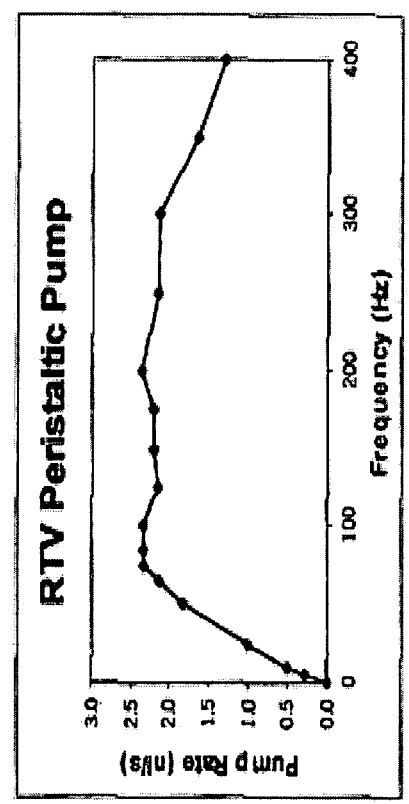
FIG. 8B is a graph illustrating the pump throughput as a function of actuation frequency in accordance with one or more embodiments of the invention.

Multiplexing schemes have been developed to allow individual addressing of these valves. FIG. 8A illustrates a schematic diagram of a nanoliter pump in accordance with one or more embodiments of the invention. Three valving control channels 802 cross a single fluid channel 804. By actuating the valves in phase, fluid is pumped through the chip. The graph illustrated in FIG. 8B shows the pump throughput as a function of actuation frequency.

These valves and pumps may be used to make a variety of chips, including an integrated fluorescence activated cell sorter [32,33], a rotary pump [34], and a 12 nanoliter PCR machine [35]. The technology may be used to make highly integrated chips with thousands of valves and hundreds of individually addressable chambers [31]. It may also be successfully applied to large scale screening of protein crystallization growth conditions, a major hurdle in structural genomics projects [36].

Embodiments of the invention provides new chip components that implement the basic tools for biology, and these components enable the development of true lab-on-a-chip devices for the life sciences.

Thus, as described above, embodiments of the invention provide for the fabrication of highly functional analysis and sensor systems. By using microfluidics, reagents or analytes can be moved from sensor to sensor, surfaces can be selectively functionalized, and calibration tests can be performed, all on one monolithic chip with transparent fluid flow channels and little or no worries about materials compatibility between the fluidic and the opto-electronic platforms. As the fluidic capabilities improves, the need for on-chip monitoring and sensing rapidly increases. The present invention enables the performance of excitation spectroscopy, Raman spectroscopy, refractive index determination, and absorption spectroscopy on few molecules within a well-characterized optical cavity.

Highly Integrated Plumbing

Figure 9:
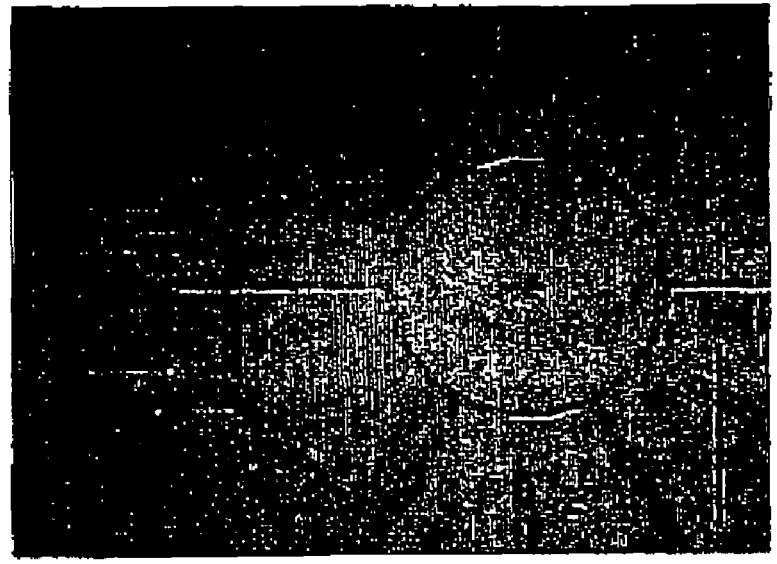
FIG. 9 is a device illustrating a fluidic channel arranged in a circle, with inputs and outputs, and permits the user to pump fluid in a closed loop in accordance with one or more embodiments of the invention.
Figure 9:
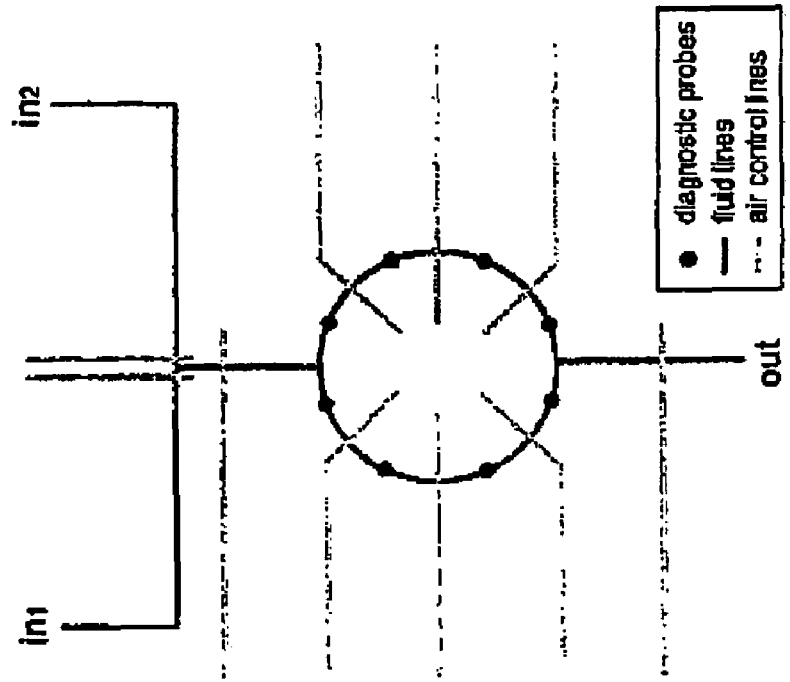

The Multilayer Soft Lithography process described above may be applied to the fabrication of integrated valves. Higher functionality is also attainable by integrating many valves on a single chip. Perhaps the most simple multi-valve construction is of a peristaltic pump: three consecutive valves [30]. These pumps can achieve throughputs of a few nanoliters per second, sufficient for most if not all lab on a chip applications. The next level of integration can be seen in the rotary mixing chip [34]. This device, illustrated in FIG. 9, has the fluidic channel arranged in a circle, with inputs and outputs, and permits the user to pump fluid in a closed loop. This device has three fluid input/output ports and approximately 10 valves. Even this low level of complexity results in a device with many applications. For example, such a device may be used for rapid mixing [34], acceleration of chemical kinetics [32], and as an ultra-low volume PCR machine [35].

Logical Flow

Figure 10:
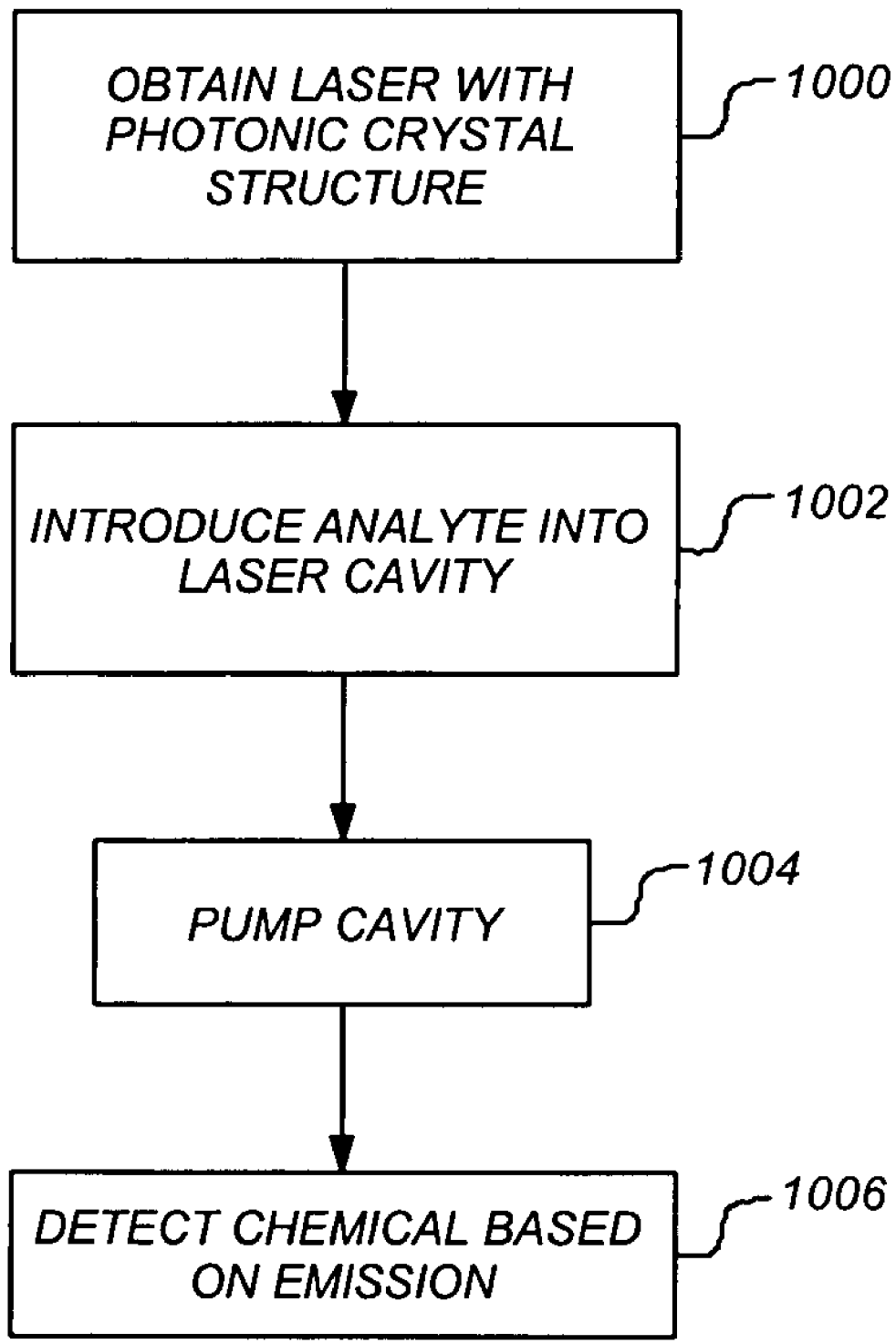
FIG. 10 is a flow chart illustrating the detection of a chemical in accordance with one or more embodiments of the invention.

FIG. 10 is a flow chart illustrating the detection of a chemical in accordance with one or more embodiments of the invention. FIG. 11 illustrates a structure used for detecting a chemical in accordance with the flow chart of FIG. 10. At step 1000, a phoronic crystal laser 1100 is obtained. The geometry of the cavity 1102 of the laser 1100 is based on a photonic crystal lattice structure having a defect. As described above, the defect may be a single defect hole in the photonic crystal lattice structure. Further, the lattice structure may rely on altering the length of one or more holes in the lattice structure to break the symmetry of the geometry of the cavity 1102. Such an alteration effectively provides a fractional edge dislocation.

At step 1002, an analyte is introduced directly into the high optical field of the laser cavity 1102. The analyte may be introduced by immersing the cavity 1102 into the analyte. Alternatively, the analyte may be introduced by integrating the cavity 1102 with a microfluidic system.

At step 1004, the laser cavity 1102 is pumped (ie., by pump 1104). The presence of the chemical in the analyte may then be detected based on the emission from the laser at step 1006. The presence of the chemical may be detected by measuring a refractive index of the analyte by determining a wavelength shift in the emission from the laser 1100 when the analyte is introduced into the laser cavity 1102. Alternatively, the detection may be based on absorption spectroscopy where the cavity 1102 of the laser 1100 provides a predetermined spectral signature (configured for a particular chemical) and the detection is based on whether and what wavelength of light is emitted from the cavity 1102. In yet another embodiment, multiple laser cavities 1102 may be densely integrated, with each cavity 1102 configured for a different predetermined spectral signature such that many reactions can be simultaneously monitored. The analyte is introduced into all of the cavities 1102 which are pumped to determine the presence of the chemical in the analyte.

A cavity enhanced photodetector 1106 may also be used to receive the emission from the laser 1100. The photodetector 1106 may provide/convett the received emission into an electrical signal (e.g., current or voltage) that is proportional to light within a resonance range. The electrical signal may then be used to detennine the length of the cavity 1102 and a refractive index within the cavity 1102 to detect the chemical.

In addition to the above, a molecule within the analyte may be highlighted using a dye (e.g., flourescent dye). A visible signal may then be observed when the molecule approaches the cavity of the laser and the resulting emission may be evaluated accordingly.

Also, the laser may be tuned to provide for the detection of chemicals. In this regard, a liquid crystal may be in the cavity. An external voltage may be applied to orient the crystal a particular way. This orientation effectively tunes the laser to a particular output that can be evaluated/analyzed.

REFERENCES

[1] T. F. Krauss, R. M. De La Rue and S. Brand, Nature, 383, pp. 699–702 (1996).

[2] H. Mabuchi, M. Armen, B. Lev, M. Loncar, J. Vuckovic, H. J. Kimble, J. Preskill, M. Roukes, A. Scherer, Quant. Info. and Comput., 1, pp. 7–12 (2001).

[3] E. Miyai and K. Sakoda, Jap. J. of Appl. Phys., 41, pp. L694–L696, (2002).

[4] J. Vuckovic, M. Loncar, H. Mabuchi and A. Scherer, Phys. Rev. E., 65, 016608 (2001).

[5] T. Yoshie, J. Vuckovic, A. Scherer, H. Chen and D. Deppe, Appl. Phys. Lett., 79, pp. 4289–4291 (2001).

[6] H. G. Park, J. K. Hwang, J. Huh, H. Y. Ryu and Y. H. Lee, Appl. Phys. Lett., 79, pp. 3032–3034 (2001).

[7] H. Y. Ryu, S. H. Kim, H. G. Park, J. K. Hwang, Y. H. Lee, Appl. Phys. Lett., 80}, pp. 3883–3885 (2002).

[8] M. Loncar, T. Yoshie, A. Scherer, P. Gogna and Y. Qiu, Appl. Phys. Lett., 81, pp. 2680–2682 (2002).

[9] T. Yoshie, O. B. Schcekin, H. Chen, D. G. Deppe and A. Scherer, Elect. Lett., 38}, pp. 967–968 (2002).

[10] 0. J. Painter, A. Husain, A. Scherer, J. D. O'Brien, I. Kim and P. D. Dapkus, J. of Lightw. Tech.}, 17, pp. 2082–2088 (1999).

[11] J. Vuckovic, M. Loncar, H. Mabuchi and A. Scherer, IEEE J. of Quant. Elect., 38, pp. 850–856 (2002).

[12] K. Okamoto, M. Loncar, T. Yoshie, A. Scherer, Y. Qiu and P. Gogna, Appl. Phys. Lett., in press.

[13] 0. Painter, J. Vuckovic and A. Scherer, JOSA B, 16, pp. 275–285 (1999).

[14] D. J. Harrison, K. Fluri, K. Seiler, Z. H. Fan, C. S. Effenhauser and A. Manz, "Micromachining a miniaturized capillary electrophoresis-based chemical-analysis system on a chip", Science 261, 895 (1993).

[15] N. H. Chiem and D. J. Harrison, "Monoclonal antibody binding affinity determined by microchip-based capillary electrophoresis", Electrophoresis 19, 3040 (1998).

[16] J. F. Li, J. J. Kelly, I. Chemusevich, D. J. Harrison and P. Thibault, "Separation and identification of peptides from gel-isolated membrane proteins using a microfabricated device for combined capillary electrophoresis/nano-electrospray mass spectrometry", Anal. Chem. 72, 599 (2000).

[17] C. S. Effenhauser, G. J. M. Bruin and A. Paulus, "Integrated capillary electrophoresis on flexible silicone microdevices: Analysis of DNA restriction fragments and detection of single DNA molecules on microchips", Anal. Chem. 69, 3451 (1997).

[18] S. C. Jacobson, R. Hergenroder, L. B. Koutny and J. M. Ramsey, "High speed separations on a microchip", Anal. Chem. 66, 1114 (1994).

[19] H. P. Chou, C. Spence, A. Scherer and S. R. Quake, "A microfabricated device for sizing and sorting DNA molecules", Proc. Nat'l. Acad. Sci. 96, 11 (1999).

[20] H. Morgan, N. G. Green, M. P. Hughes, W. Monaghan and T. C. Tan, "Large area traveling-wave dielectrophoresis particle separator", J. Micromech. Microeng. 7, 65 (1997).

[21] S. Fiedler, S. G. Shirley, T. Schnelle, and G. Fuhr, "Dielectrophoretic sorting of particles and cells in a microsystem", Anal. Chem. 70, 1909 (1998).

[22] J. P. Brody and P. Yager, "Low Reynolds number microdevices", In Proc. Of Solid State Sensor and Actuator Workshop, pp. 105–8. Hilton Head, June 1996.

[23] M. U. Kopp, A. J. de Mello and A. Manz, "Chemical amplification: continuous flow PCR on a chip", Science 280, 1046 (1998).

[24] L. C. Waters, S. C. Jacobson, N. Kroutchinina, J. Khandurina, R. S. Foote and J. M. Ramsey, "Microchips devices for cell lysis, multiplex PCR amplification, and electrophoretic sizing", Anal. Chem. 70, 158 (1998).

[25] P. H. Li and D. J. Harrison, "Transport, manipulation and reaction of biological cells on-chip using electrokinetic effect", Anal. Chem. 69, 1564 (1997).

[26] A. G. Hadd, D. E. Raymond, J. W. Halliwell, S. C. Jacobson and J. M. Ramsey, "Microchip device for performing enzyme assays", Anal. Chem. 69, 3407 (1997).

[27] A. G. Hadd, S. C. Jacobson and J. M. Ramsey, "Microfluidic assays of acetylcholinesterase inhibitors", Anal. Chem. 71, 5206 (1999).

[28] N. H. Chiem and D. J. Harrison, "Microchip-based capillary electrophoresis for immunoassays: analysis of monoclonal antibodies and theophylline", Electrophoresis 19, 3040 (1998).

[29] A. Y. Fu, C. Spence, A. Scherer, F. H. Arnold and S. R. Quake, "A microfabricated fluorescence-activated cell sorter", Nature Biotech. 18, 309 (2000).

[30] M. A. Unger, H. P. Chou, T. Thorsen, A. Scherer and S. R. Quake, "Monolithic Microfabricated Valves and Pumps by Multilayer Soft Lithography", Science 288, 113 (2000).

[31] T. Thorsen, S. J. Maerkl, and S. R. Quake, "Microfluidic Large Scale Integration", Science 298, 580 (2002).

[32] S. R. Quake and A. Scherer, "From Micro to Nano Fabrication with Soft Materials", Science 290, 1536 (2000).

[33] A. Fu, H. P. Chou, C. Spence, F. Arnold and S. R. Quake, "An integrated microfabricated cell sorter", Anal Chem., 74, 2451 (2002).

[34] H. P. Chou, M. A. Unger, A. Scherer and S. R. Quake, "A Microfabricated Rotary Pump", Biomedical Microdevices 3, 323 (2001).

[35] J. Liu, M. Enzelberger, and S. R. Quake, "A nanoliter rotary device for PCR", Electrophoresis 23, 1531 (2002).

[36] C. Hansen, E. Skordalakes, J. M. Berger, and S. R. Quake, "A robust and scalable microfluidic metering method that allows protein crystal growth by free interface diffusion", Proc. Nat'l. Acad. Sci. 99, 16531 (2002).

CONCLUSION

This concludes the description of the preferred embodiment of the invention. In summary, there are many opportunities which present themselves once one has the opportunity to pump and probe sub-femtoliter sample volumes. The present invention presents lasers that may only support one or two modes, whose frequency can be precisely designed. Accordingly, it is possible to avoid the mode-hopping problems commonly associated with larger microcavity semiconductor lasers. The invention also provides for a tool-kit to make monolithic sensors using photonic crystal nanocavity lasers, that may result in the radical reduction of size of spectroscopic systems. The flexibility afforded by the ability to emit, confine, direct and monitor light within planar photonic crystals enables the definition of ultra-small, robust optical interrogation systems which can be integrated with modem microfluidics.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A system for detecting a chemical comprising:
a laser having a cavity;
a photonic crystal lattice structure having a defect that defines a geometry of the cavity;
an analyte that is introduced directly into an optical field of the cavity;
an emission from the laser that is used to detect a presence of a chemical in the analyte.

2. The system of claim 1, wherein the defect is a single defect hole in the photonic crystal lattice structure.

3. The system of claim 1, wherein the photonic crystal lattice structure further relies on altering a length of one or more holes in the lattice structure to break a symmetry of the geometry of the cavity.

4. The system of claim 1, wherein the analyte is introduced by immersing the cavity into the analyte.

5. The system of claim 1, wherein the analyte is introduced by integrating the cavity with a microfluidic system.

6. The system of claim 1, wherein the presence of the chemical is detected by measuring a refractive index of the analyte by determining a wavelength shift in the emission from the laser when the analyte is introduced into the field of the cavity.

7. The system of claim 1, further comprising a cavity enhanced photodetector configured to receive the emission from the laser, wherein:

the photodetector provides an electrical signal proportional to light within a resonance range; and the electrical signal may be used to determine a length of the cavity and a refractive index within the cavity to detect the chemical.

8. The system of claim 1, further comprising a dye used to highlight a molecule within the analyte, wherein a visible signal is observed when the molecule approaches the cavity of the laser.

9. The system of claim 1, wherein the cavity of the laser provides a predetermined spectral signature for a particular chemical and the presence of the chemical in the analyte is detected based on a wavelength of light emitted from the cavity.

10. The system of claim 9, wherein multiple laser cavities are integrated, with each cavity having a different predetermined spectral signature and many reactions can be simultaneously monitored.

11. A method for detecting a chemical comprising:

obtaining a photonic crystal laser wherein a geometry of a cavity of the laser is based on a photonic crystal lattice structure having a defect;

introducing an analyte directly into a high optical field of the cavity;

pumping the cavity; and detecting a presence of a chemical in the analyte based on an emission from the laser.

12. The method of claim 11, wherein the defect is a single defect hole in the photonic crystal lattice structure.

13. The method of claim 11, wherein the photonic crystal lattice structure further relies on altering a length of one or more holes in the lattice structure to break a symmetry of the geometry of the cavity.

14. The method of claim 11, wherein the analyte is introduced by immersing the cavity into the analyte.

15. The method of claim 11, wherein the analyte is introduced by integrating the cavity with a microfluidic system.

16. The method of claim 11, wherein the step of detecting a presence of the chemical comprises measuring a refractive index of the analyte by determining a wavelength shift in the emission from the laser when the analyte is introduced into the optical field of the cavity.

17. The method of claim 11, wherein the detecting step further comprises receiving the emission from the laser into a cavity enhanced photodetector, wherein:

the photodetector provides an electrical signal proportional to light within a resonance range; and the electrical signal may be used to determine a length of the cavity and a refractive index within the cavity to detect the chemical.

18. The method of claim 11, further comprising:

highlighting a molecule within the analyte using a dye, and observing a visible signal when the molecule approaches the cavity of the laser.

19. The method of claim 11, wherein the cavity of the laser provides a predetermined spectral signature for a particular chemical and the detecting step is based on a wavelength of light emitted from the cavity.

20. The method of claim 19, wherein multiple laser cavities are integrated, with each cavity having a different predetermined spectral signature and many reactions can be simultaneously monitored.

21. An apparatus for detecting a chemical comprising:

means for obtaining a photonic crystal laser wherein a geometry of a cavity of the laser is based on a photonic crystal lattice structure having a defect;

means for introducing an analyte directly into an optical field of the cavity;

means for pumping the cavity; and means for detecting a presence of a chemical in the analyte based on an emission from the laser.

22. The apparatus of claim 21, wherein the defect is a single defect hole in the photonic crystal lattice structure.

23. The apparatus of claim 21, wherein the photonic crystal lattice structure further relies on altering a length of one or more holes in the lattice structure to break a symmetry of the geometry of the cavity.

24. The apparatus of claim 21, wherein the analyte is introduced by immersing the cavity into the analyte.

25. The apparatus of claim 21, wherein the analyte is introduced by integrating the cavity with a microfluidic system.

26. The apparatus of claim 21, wherein the means for detecting a presence of the chemical comprises means for measuring a refractive index of the analyte by determining a wavelength shift in the emission from the laser when the analyte is introduced into the optical field of the cavity.

27. The apparatus of claim 21, wherein the means for detecting a presence of a chemical further comprises means for receiving the emission from the laser into a cavity enhanced photodetector, wherein:

the photodetector provides an electrical signal proportional to light within a resonance range; and the electrical signal may be used to determine a length of the cavity and a refractive index within the cavity to detect the chemical.

28. The apparatus of claim 21, further comprising:

means for highlighting a molecule within the analyte using a dye; and means for observing a visible signal when the molecule approaches the cavity of the laser.

29. The apparatus of claim 21, wherein the cavity of the laser provides a predetermined spectral signature for a particular chemical and the presence of the chemical in the analyte is detected based on a wavelength of light emitted from the cavity.

30. The apparatus of claim 29, wherein multiple cavities are integrated, with each cavity having a different predetermined spectral signature and many reactions can be simultaneously monitored.

* * * * *

UNITED STATES PATENT AND TRADEMARK OFFICE
CERTIFICATE OF CORRECTION

PATENT NO. : 7,079,240 B2 Page 1 of 1
APPLICATION NO. : 10/794071
DATED : July 18, 2006
INVENTOR(S) : Axel Scherer et al.

It is certified that error appears in the above-identified patent and that said Letters Patent is hereby corrected as shown below:

Column 1, line 25, after "Foundation" insert -- and Grant No. 49620-01-6-0497 awarded by the Air Force--.

Signed and Sealed this

Fourteenth Day of November, 2006

JON W. DUDAS
*Director of the United States Patent and Trademark Office*